United States Patent [19]
Larsen et al.

[11] Patent Number: 6,163,715
[45] Date of Patent: *Dec. 19, 2000

[54] DIRECT TO DIGITAL OXIMETER AND METHOD FOR CALCULATING OXYGENATION LEVELS

[75] Inventors: Michael T. Larsen, Wauwatosa; James L. Reuss, Waukesha, both of Wis.

[73] Assignee: Criticare Systems, Inc., Waukesha, Wis.

[*] Notice: This patent is subject to a terminal disclaimer.

[21] Appl. No.: 09/201,942

[22] Filed: Dec. 1, 1998

Related U.S. Application Data

[63] Continuation-in-part of application No. 08/683,617, Jul. 17, 1996, Pat. No. 5,842,981.

[51] Int. Cl.[7] ........................................................ A61B 5/00
[52] U.S. Cl. ..................................................................... 600/323
[58] Field of Search .................................... 600/310, 322, 600/323, 330

[56] References Cited

U.S. PATENT DOCUMENTS

| | | |
|---|---|---|
| 3,638,640 | 2/1972 | Shaw . |
| 3,799,672 | 3/1974 | Vurek . |
| 3,847,483 | 11/1974 | Shaw et al. . |
| 3,998,550 | 12/1976 | Konishi et al. . |
| 4,086,915 | 5/1978 | Kofsky et al. . |
| 4,167,331 | 9/1979 | Nielsen . |
| 4,266,554 | 5/1981 | Hamaguri . |
| 4,357,105 | 11/1982 | Loretz . |
| 4,407,290 | 10/1983 | Wilber . |
| 4,446,871 | 5/1984 | Imura . |
| 4,740,080 | 4/1988 | Donohue et al. . |
| 4,773,422 | 9/1988 | Isaacson et al. . |
| 4,807,631 | 2/1989 | Hersh et al. . |
| 4,819,752 | 4/1989 | Zelin ........................................ 600/322 |
| 4,854,699 | 8/1989 | Edgar, Jr. . |
| 5,190,038 | 3/1993 | Polson et al. . |
| 5,348,004 | 9/1994 | Hollub . |
| 5,349,519 | 9/1994 | Kaestle . |
| 5,355,880 | 10/1994 | Thomas et al. . |
| 5,398,680 | 3/1995 | Polson et al. . |
| 5,413,100 | 5/1995 | Barthelemy . |
| 5,533,507 | 7/1996 | Potratz .................................... 600/330 |
| 5,842,981 | 12/1998 | Larsen et al. ........................... 600/323 |

*Primary Examiner*—Eric F. Winakur
*Attorney, Agent, or Firm*—Reinhart, Boerner, Van Deuren, Norris & Rieselbach, s.c.

[57] ABSTRACT

An oximeter for non-invasively measuring the oxygen saturation in blood with increased speed and accuracy is disclosed. The oximeter includes a number of features which increase the functionality of the device including: a dynamic range control for monitoring a range of inputs from low level signals encountered in fetal and other applications to typical or high level signals; light emitting devices of different wavelengths for filtering noise and providing additional medial monitoring functions; and an improved method for calculating the oxygenation levels without the need to take peak and valley measurements. The device includes a sensor unit which can be attached to a patient and an oximeter which determines the oxygen saturation in the blood based on signals received from the sensor. The sensor can include light emitting devices in three or more wavelengths to provide additional functions. In the present invention, the detected signal is immediately converted to a digital value.

19 Claims, 1 Drawing Sheet

DIRECT TO DIGITAL OXIMETER AND METHOD FOR CALCULATING OXYGENATION LEVELS

This is a continuation-in-part of application Ser No. 08/683,617 filed on Jul. 17, 1996 is now, U.S. Pat. No. 5,842,981.

The present invention is concerned generally with an improved oximeter for non-invasively measuring arterial oxygen saturation. More particularly, this invention is concerned with an improved method for direct digital signal formation from input signals produced by a sensor device which is connected to the oximeter.

In all oximeters, input signals are received from a sensor device which is directly connected to the blood-carrying tissue of a patient, such as a finger or ear lobe. The sensor device generally consists of a red LED, an infrared LED, and one or two photodetectors. Light from each LED is transmitted through the tissue, and the photodetectors detect the amount of light which passes through the tissue. The detected light consists of two components for each bandwidth. An AC component represents the amount of pulsating blood detected, while the DC component represents the amount of non-pulsating blood. Therefore, four separate components of detected light are examined in order to determine the arterial oxygen saturation: red DC, red AC, infrared DC and infrared AC. The amount of light detected is then used to determine the oxygen saturation in the blood of the patient based on the following equation:

(IR(AC)/IR(DC))/(Red(AC)/Red(DC))

In a traditional oximeter, the sensor output signal is converted to an analog voltage and then separated into infrared and red components. Some oximeters further separate the AC and DC components. Separate analog circuits are then used to sample, demultiplex, and filter these signals. In these systems, therefore, it is necessary to carefully match the analog components to minimize errors which can result from differences in gain or frequency response in the two circuits. Furthermore, because of the need to carefully match hardware for each analog input circuit, and the increased probability of errors when additional analog channels are added, traditional oximeters are generally limited to two analog inputs.

Additionally, the analog circuitry employed in traditional oximeters is generally insufficient to accurately detect low level signals. Therefore, these oximeters are generally ineffective for monitoring fetal conditions, as well as for use with patients with thick or very dark skin. Furthermore, the methods used in prior art oximeters for measuring oxygenation levels rely heavily on pulse detection and peak-valley measurements which are highly susceptible to variations due to motion artifact noise.

The instant invention improves on the analog signal processing employed in prior art oximeters by receiving input current signals from at least two and preferably three light emitting devices of different wavelengths and converting these input signals directly to digital voltage values, without first converting to analog voltages or separating the signals. This is accomplished by using a charge digitizing analog to digital converter with sufficient range to represent the large DC signals and sufficient resolution to represent the small AC signals. This charge digitizing converter employs a current integrator as the front stage, which tends to average and filter input noise. This is an improvement over the analog current to voltage conversion used in traditional oximeters, which tend to amplify noise.

Once the input current is converted to a digital voltage value, all input signals are processed along the same digital hardware path, instead of the separate analog hardware paths required by the traditional method. This system eliminates the need to match analog hardware components, and therefore further reduces potential errors. Furthermore, once the signals are digitized, a microprocessor can perform all of the signal processing, demultiplexing, and filtering steps required by traditional oximeters. This reduction in the analog signal processing stage increases both the speed and accuracy of the oximeter, decreases cost by eliminating expensive analog components, and reduces the size of the oximeter by eliminating physically large analog components.

In another aspect of the invention, a method for analyzing oxygenation levels without the need for pulse detection and peak-valley measurements is also disclosed. The method comprises the steps of storing vectors of contiguous, paired infrared and red data samples over a period of time, using a least-squares minimization method for determining an infrared to red ratio, and determining a noise metric for filtering noise from the resultant oxygenation calculations. The noise metric substantially filters noise due to motion artifact, such as source: detector geometry variations and respiration noise, thereby providing a more accurate oxygenation level reading.

In a further improvement, additional wavelengths can be added to the oximeter to improve noise filtering or add medical monitoring functions to the oximeter. Because all signal conversion is time-multiplexed through a single analog to digital converter circuit, a third or further wavelengths can be easily and inexpensively added to the sensor and device. The additional wavelengths can be used in a number of applications which increase the accuracy of the oximeter or provide additional monitoring functions, including: noise detection; dyshemoglobin detection and/or measurement; and indicator dye measurement.

Due to the ability of the digital circuitry of the present invention to process low level current input signals and to filter noise components and the additional noise filtering functions disclosed, the oximeter can be used to accurately monitor oxygenation levels which were previously difficult to monitor, including fetal oxygenation levels and the oxygenation levels of dark and thick skinned patients. In one particular embodiment the dynamic range of the analog to digital converter may be optimized to match the input signal range.

It is therefore an object of this invention to provide an improved method for non-invasively measuring fluid parameters.

It is another object of this invention to provide an improved method for measuring arterial blood saturation.

It is another object of the invention to provide improved speed and accuracy in the measurements provided by oximeters.

It is another object of the invention to provide a direct analog to digital conversion of the input current signal with sufficient range to measure large DC signals and enough resolution to represent small AC signals so that accurate measurements can be made with reduced analog signal processing.

It is another object of the invention to provide a reduction in potential errors by directly converting the input current signal to a digital voltage signal, thereby bypassing the current to voltage conversion step which can amplify noise.

It is another object of the invention to provide a reduction in potential errors by processing all signals along one digital hardware path, thereby eliminating the need for matched analog components.

It is another object of the invention to provide an improved oximeter having a reduced number of electronic circuit components.

It is still another object of the invention to provide a reduction in the size of oximeters by eliminating physically large analog components.

It is yet a further object of the invention to provide an improved method and system for directly converting to digital signal form at least two signals from light emitting devices of different wavelengths.

It is another object of the invention to provide an improved method for filtering noise from oxygenation level calculations.

It is yet another object of the invention to provide a dynamic range control for calculating oxygenation levels in a plurality of signal range levels.

It is still another object of the invention to provide an improved oximeter capable of monitoring a wide range of patients.

It is another object of the invention to provide a reduction in the size and cost of detecting more than two wavelengths in oximeters.

These and other object and advantages of the invention, together with the organization and manner of operation thereof, will become apparent from the following detailed description when taken in conjunction with the accompanying drawings described below.

DETAILED DESCRIPTION OF THE PREFERRED EMBODIMENT

Figure 1:
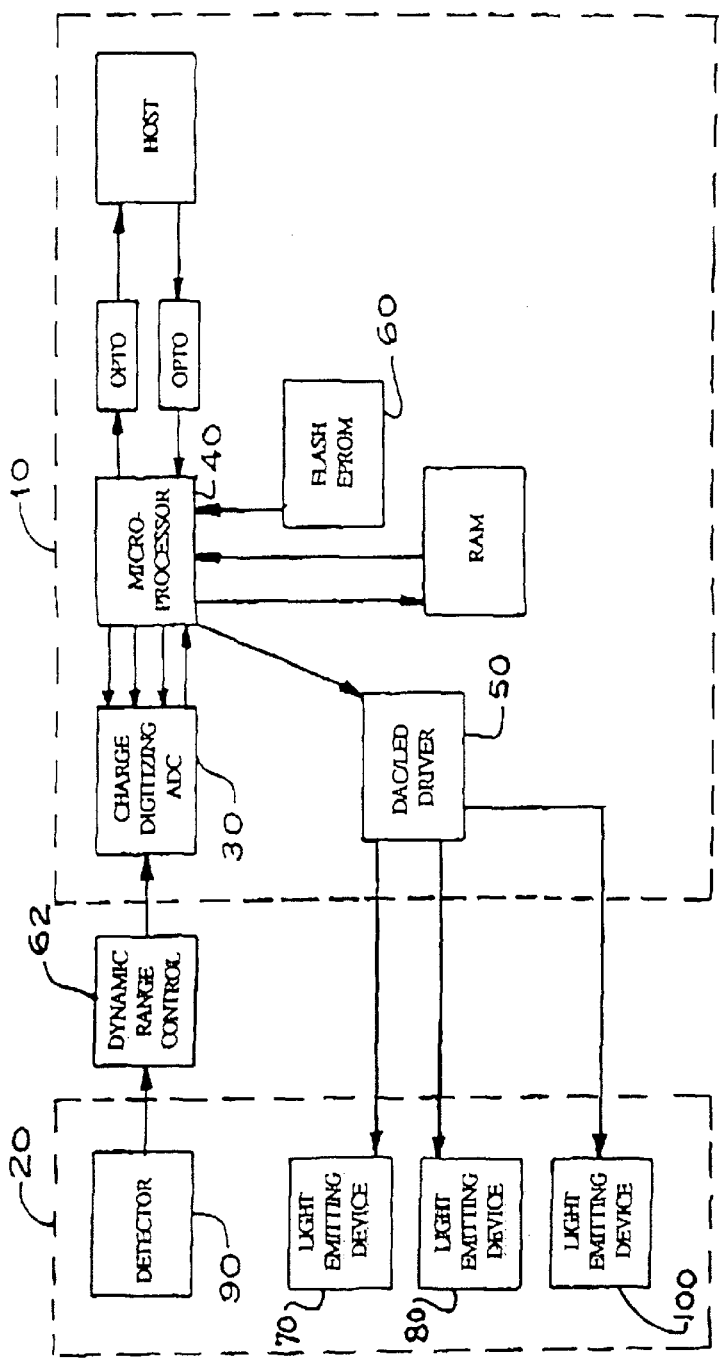
FIG. 1 illustrates a block diagram of the direct to digital oximeter as connected to a sensor device.

A block diagram of a direct to digital oximeter 10 constructed in accordance with the invention, along with an external sensor device 20 is shown in FIG. 1. The direct to digital oximeter 10 comprises a charge digitizing analog to digital converter 30, a microprocessor 40, a digital to analog converter/LED driver 50, and a flash EPROM 60. In order to achieve sufficient accuracy, the charge digitizing analog to digital converter 30 preferably converts the input analog signal to a digital signal of at least 20 bits.

Figure 2:
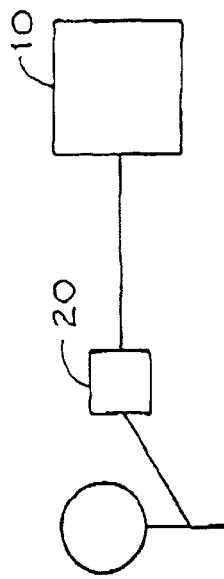
FIG. 2 illustrates the sensor device and direct to digital oximeter connected to a patient.

In a preferred embodiment (see FIG. 2) the sensor 20 is attached to a blood-carrying tissue sample, such as the finger or ear lobe of a patient. Here, the sensor 20 is shown to consist of three light emitting devices 70, 80, and 100 and a single photodetector 90, but the sensor can include two or more light emitting devices of different wavelengths and an associated plurality of photodetectors. Furthermore, although LEDs are commonly used in circuits of this type, the light emitting devices can be laser diodes, white light sources, or other suitable devices. To perform traditional pulse oximetry, however, the sensor 20 comprises a red LED 70 and an infrared LED 80.

The LED's 70 and 80 are driven by digital signals from the microprocessor 40. These digital signals are converted to analog voltages by means of the digital to analog converter/LED driver 50. Light from the LED's 70 and 80 is transmitted through the tissue sample, and is detected by the photodetector 90, which produces an analog current signal with an amplitude proportional to the amount of light detected in each bandwidth. The current signal from the photodetector 90 is then digitized with 20 bits of resolution by the charge digitizing analog to digital converter 30, and is sent to the microprocessor 40. Demultiplexing, ambient interference identification and elimination, and signal filtering are performed by means of digital signal processing software routines in the microprocessor 40. Once the signals are processed, the microprocessor 40 calculates the value of the ratio (IR(AC)/IR(DC))/(Red(AC)/Red(DC))

where the DC component represents the non-pulsating blood flow, and the AC component indicates the pulsatile blood flow. The microprocessor 40 then determines the absolute arterial oxygen saturation by comparing the result to the value stored in a look-up table in flash EPROM 60.

In one preferred embodiment, the dynamic range of the analog to digital converter is optimized to match the input signal range, thereby providing accurate monitoring over a wide range of input signals. To optimize the dynamic range, the output of the photodetector 90 is initially read to determine the strength of the input signal. If the signal is in a normal or high operating range, a dynamic range control 62 (FIG. 2) is switched into the circuit to reduce the signal amplitude, preventing saturation of the analog to digital converter 30. The dynamic range control 62 preferably comprises a current divider under software control, and is inserted between the photodetector 90 and the analog to digital converter 30. The dynamic range control 62 reduces the current input level by a predetermined amount. In situations where the photodetector 90 output is low (e.g., very dark skin, a thick tissue site, and/or reflectance mode monitoring), the software detects the low digitized signal intensity and switches out the current divider, narrowing the dynamic range and effectively raising the signal gain. While one particular method of providing a dynamic range control is shown, it will be apparent to one of ordinary skill in the art that the dynamic range control could be provided in a number of ways including amplifying a low signal to an expected higher level or reducing the charge integration time of the charge digitizing converter. Furthermore, the dynamic range control may be implemented after current:voltage conversion for a voltage-input analog to digital converter. Additionally, either a fixed or variable reduction might be implemented in the dynamic range control.

In some applications, it is desirable to add at least one additional wavelength to the sensor 20 to improve the accuracy of the oximetry measurements or to provide additional medical monitoring functions to the oximeter 10. In this case, the light emitting device 100 is added to the sensor 20, and related detector circuitry is added to the photodector 90. Because all signal conversion is time-multiplexed through a single analog to digital converter circuit 30, the only additional circuitry required to add a third or further wavelengths to the oximeter 10 is a driver to drive the additional light emitting devices of the sensor. Preferably, the light emitting devices 70, 80, and 100 are driven by a time-multiplexed digital to analog converter 50, controlled by a software-driven gate. However, it will be apparent to one of ordinary skill in the art that a pulse width modulated (PWM) output could also be used. The applications of the additional wavelength(s) in the sensor 20 include, but are not limited to: noise detection; dyshemoglobin detection and/or measurement; and indicator dye measurement.

A noise reference signal can facilitate the elimination of noise from a potentially compromised signal source. In pulse oximetry, this can be accomplished by tracking the absorbance of light at a wavelength (e.g., green) which is unaffected by the relative concentrations of different hemoglobin forms, which absorb primarily in the red. The resultant signal is neutral in the absence of noise, but represents fluctuations in intensity due to changes in emitter:detector geometry or other noise sources. The noise reference signal can be employed in a number of known mathematical approaches to noise elimination, including adaptive signal processing.

Dyshemoglobins occur when the hemoglobin molecule binds with another molecule besides oxygen, and include methemoglobins, sulfhemoglobins, and carboxyhemoglobins. A form which is of particular clinical significance is carboxyhemoglobin, the combination of carbon monoxide with hemoglobin. Carbon monoxide poisoning is a significant cause of morbidity and mortality. Acute cases are often associated with smoke inhalation at the scene of a fire, but chronic poisoning, wherein a patient presents with "flu" symptoms, may be more insidious. Conventional pulse oximeters cannot readily distinguish carboxyhemoglobin from oxyhemoglobin, resulting in a falsely reassuring oxygen saturation reading. One approach which has been utilized (see U.S. Pat. Nos. 4,167,331, 5,355,880, and 5,413,100, which are hereby incorporated in their entirety) requires a choice of wavelengths near three isobestic points (approximately 580, 650, and 800 nm). However, if detection without exact quantification is sufficient (e.g., to generate a warning), the addition of an 800 nm wavelength (isobestic between reduced and oxygenated hemoglobin) to the basic oximeter is sufficient to identify the presence of carboxyhemoglobin.

Indicator dyes are introduced as part of several monitoring procedures, including dye dilution cardiac output assessment. For example, U.S. Pat. No. 5,494,031, which is hereby incorporated in its entirety, discloses the use of indocyanine green dye for this purpose, with non-invasive concentration measurement utilizing photoplethysmography. By adding a wavelength of substantially 800 nm to the pulse oximeter sensor, along with known analysis software or methods, and utilizing the infrared wavelength (940 nm) of the pulse oximeter sensor as a reference, a cardiac output assessment function is added to a pulse oximeter.

Although the oximeter has been described employing three wavelengths, it will be apparent to one of ordinary skill in the art that two or more of the noted features could be added simultaneously by adding additional light emitting devices and associated software to the oximeter.

In another embodiment of the invention, vectors of infrared and red signal data are stored and used by the microprocessor 40 to determine the arterial oxygenation level. In this embodiment, the arterial oxygenation levels are determined as a ratio of observed red ac values ($R^{obs}_{ac}$) to observed infrared ac values ($I^{obs}_{ac}$). A noise metric determined by comparing the observed red signal to a predicted red signal is employed to filter the noise components from the signal, thereby obtaining a more accurate oxygenation reading.

Following are the steps used to determine the oxygenation saturation level. Assuming for the moment ideal conditions, $$I_{dc} = LP(I)$$
$$I_{ac} = I - I_{dc}$$
$$R_{dc} = LP(R)$$
$$R_{ac} = R - R_{dc}$$

where capital letters are employed to indicate vectors of L contiguous data samples ($I=\{i_1, i_2, \ldots, i_L\}$) equally spaced in time with an appropriate sampling rate. Vector length can impact stability of the I:R ratio calculation as well as ability to detect noise in a timely and reliable fashion. The critical timing has been shown experimentally to be the time to slew between minimum and maximum absorbance (caused by the leading edge of the arterial blood bolus), only 100–200 msec in a hemodynamically effective pulse.

The ac subscripts indicate a high-passed or unbiased pulsatile component (variation in intensity), and the dc subscripts indicate a low-passed, relatively long-term trend, or bias (the overall intensity level). Here LP( ) is assumed to have linear phase shift, permitting derivation of the high-passed signal by subtracting the low-passed version from the original. This filtering may be accomplished in hardware, but would be performed by software in the digital oximeter.

Given R and I, it is known to obtain the $SpO_2$ value by taking the scaled ratio of infrared and red pulse amplitudes, employing an empirically derived proportionality expressed here as an arbitrary function K:

$$SpO_2 = K\left( \frac{(\max(I_{ac}) - \min(I_{ac}))/I_{dc}}{(\max(R_{ac}) - \min(R_{ac}))/R_{dc}} \right)$$

where max( ) and min( ) denote the signal maxima and minima.

However, assuming equivalent LED:detector geometry, the I and R vectors are linearly related. One vector, therefore, can be expressed as a simple linear combination (mX+b) of the other. The constant difference is the difference in the low-passed intensity or dc levels, leaving the high-passed components linearly related by the I:R ratio ρ:

$$R_{ac} = \rho I_{ac}$$

Then the formula for $SpO_2$ may be rewritten as $$SpO_2 = K\left( \frac{(\max(I_{ac}) - \min(I_{ac}))/I_{dc}}{(\max(\rho I_{ac}) - \min((\rho I)_{ac}))/R_{dc}} \right)$$
$$= K\left( \frac{(\max(I_{ac}) - \min(I_{ac}))/I_{dc}}{\rho(\max(I_{ac}) - \min((I)_{ac}))/R_{dc}} \right)$$

or just $= K((R_{dc}/I_{dc})/\rho)$

The least-squares minimization (LSM) method is employed to derive ρ from the signal data by taking $$\rho = (I_{ac} \circ R_{ac})/(I_{ac} \circ I_{ac})$$

where ∘ is used here to indicate the dot product of two vectors, yielding in this case the ratio of two scalars. (Note that it is assumed here that the LP( ) function, although applied continuously over the data, results in unbiased data vectors $I_{ac}$ and $R_{ac}$, since the LSM method actually specifies removal of the vector mean from the biased data prior to computation.) If this is not the case, it is possible to recast the calculation of p using ($I-\mu_I$) and ($R-\mu_R$) instead and still derive the I:R ratio, assuming appropriate choice of vector length.)

This calculation of $SpO_2$ is independent of pulse location and peak-valley measurements and will hereafter be called "continuous $SpO_2$ calculation". However, as will be described below, the calculation still relies upon the fact that pulsatile events takes place within the data vector extent.

The above calculations were determined under ideal conditions. To obtain an accurate signal, therefore, it is necessary to account for the noise encountered in pulse oximetry calculations. Under non-ideal conditions, the observed intensities are actually $$I^{obs}=I+N_I$$

$$R^{obs}=R+N_R$$

where $N_I$ and $N_R$ are noise components which are assumed to be unbiased (low frequency interference tends not to effect the relatively short data vectors used. An observed I:R ratio $\rho_{obs}$ is defined by $$R^{obs}{}_{ac}=\rho_{obs}I^{obs}{}_{ac}$$

where $\rho_{obs}=\rho$ in the absence of noise. Now $N_I$ and $N_R$ may be uncorrelated or correlated, and if the latter, may possess the same or different proportionality ratio as the I:R ratio $\rho$ of the desired signal components I and R. Considering the most difficult situation of correlated noise, noise possessing the same ratio as $\rho$ would not effect the LSM calculation of $\rho_{obs}$ from $I^{obs}$ and $R^{obs}$, giving $\rho=\rho_{obs}$. However, assuming a general case of $$N_R=\rho_N N_I$$

with $\rho_N \neq \rho$, the noise components must be removed or canceled to accurately calculate $\rho_{obs}$ and thence $SPO_2$ directly from $I_{obs}$ and $R_{obs}$.

Since the $SpO_2$ value represents the binding state of millions of hemoglobin molecules, as determined by relatively slow processes such as alveolar transport of molecular oxygen, pumping of blood through the circulatory system, and venous return through the capillary beds, the pulse-to-pulse variation in the $SpO_2$ level is relatively small. Motion artifact, however, tends to appear rather suddenly, induces non-linear effects on the sample-to-sample relationship between $R^{obs}{}_{ac}$ and $I^{obs}{}_{ac}$, and disturbs the observed I:R ratio. Noise attributed to motion artifact, therefore, must be filtered to obtain an accurate calculation. The noise can be quantified with a noise metric between $R^{obs}{}_{ac}$ and the predicted red signal, obtained from $I^{obs}{}_{ac}$ by assuming a constant estimated $\rho_{est}$ (derived from the recent history of $\rho_{obs}$ under low noise conditions):

$$R^{pred}{}_{ac}=\rho_{est}I^{obs}{}_{ac}$$

Letting $\Delta(\ )$ indicate a desired noise metric, $$\nu=\Delta(R^{obs}{}_{ac}, R^{pred}{}_{ac})/\alpha$$

where $\alpha$ is a normalization factor (required if the metric is not inherently normalized). The metric is defined so that $\nu$ is zero only if $\rho_{obs}=\rho$, and otherwise is positive and increasing with increasing disturbance of either or both observed intensity signals.

One distance metric is the average absolute difference between corresponding vector elements, or $$\Delta(V, W) = \left(\sum_{j=1}^{L}|v_j - w_j|\right)/L$$

which is simple to compute and may be recursively obtained. This metric, however, requires a normalization for the expected magnitude of the signals. This normalization must be obtained from $I^{obs}{}_{ac}$ and $R^{obs}{}_{ac}$ data gathered under low noise conditions (denoted $R^{est}{}_{ac}$ and $I^{est}{}_{ac}$). One example is the maximum magnitude of the two estimated signals, or $$\alpha = \left(\sum_{j=1}^{L}\max(|r_j|, |i_j|)\right)/L$$

It will be apparent to one of ordinary skill in the art that other distance metrics (including correlation) can be applied to the problem of comparing $R^{obs}{}_{ac}$ to $R^{pred}{}_{ac}$.

By empirically establishing a threshold for acceptable performance, the noise metric $\nu$, calculated at the same time as the new $\rho_{obs}$, can be used to control not only $SpO_2$ averaging but other pulse oximetry processing (such as pulse rate determination).

As pointed out above, the continuous $SpO_2$ calculation does not require determination of pulse timing. However, since it is desirable to limit the vector length (e.g., to less than one second), it will be possible in low heart rate situations to obtain data vectors containing no pulsatile event. These vectors will show less of the arterial absorbance effect which is the basis of pulse oximetry. In preferred embodiments, therefore, an ECG or other indicator is used to synchronize the data collection.

While preferred embodiments of the invention have been shown and described, it will be clear to those skilled in the art that various changes and modifications can be made without departing from the invention in its broader aspects as set forth in the claims provided hereinafter.

What is claimed is:

1. An oximeter for non-invasively measuring arterial oxygen saturation, comprising:
   a sensor including at least first and second light emitting devices for producing light in at least two wavelengths;
   at least one photodetector for detecting said light, after passing through a tissue sample containing a pulsating blood supply, and for producing an analog electrical current signal representing the absorption of each wavelength of said light;
   a dynamic range control for adjusting the range of the analog electrical current signal to an expected input range;
   an analog to digital converter for converting said analog electrical current signal to a digital voltage signal; and
   a processing unit for processing said digital voltage signal to calculate an arterial oxygen saturation.

2. The oximeter as defined in claim 1, wherein the dynamic range control comprises a current divider.

3. The oximeter as defined in claim 2, wherein the current divider is controlled by the processing unit.

4. The oximeter as defined in claim 1, wherein the processing unit is programmed to compare the analog input signal to a predetermined normal range and to switch the dynamic range control on when the analog input signal is greater than the predetermined normal range.

5. A method for calculating arterial oxygen saturation comprising the following steps:
   producing light of at least first and second wavelengths;
   directing said light at a tissue sample containing a pulsating blood supply;
   detecting said light, after passing through said tissue sample, and producing an analog electrical current signal representing the absorption rate of each wavelength of said light;
   then converting said analog electrical current signal to a digital voltage signal;
   filtering the digital voltage signal to provide a first pulsatile signal representative of the pulsatile component of the light absorbed in the first wavelength and a second pulsatile signal representative of the pulsatile component of the light absorbed in the second wavelength;

sampling the digital voltage signal to provide a first vector comprising data samples representative of light absorbed of the first wavelength;

sampling the digital voltage signal to provide a second vector comprising data samples representative of light absorbed of the second wavelength;

calculating a ratio of the first vector to the second vector; and using the ratio to determine arterial oxygen saturation.

6. The method as defined in claim 5, further comprising the steps of comparing a predicted value of at least one of the first and second wavelengths to an observed value of the same wavelength to determine a noise metric.

7. The method as defined in claim 6, further comprising the step of filtering data with the noise metric.

8. The method as defined in claim 6, further comprising the step of synchronizing the calculation with a cardiac pulse detection signal.

9. The method as defined in claim 8, in which the cardiac pulse detection signal is ECG.

10. The method as defined in claim 6, further comprising the step of using a least square minimization method to calculate the ratio.

11. A method for increasing the usable range of an oximeter, the method comprising the following steps:

producing an analog current signal indicative of a blood oxygenation level;

converting the analog current signal to an initial digital voltage signal;

reading the initial digital voltage signal;

comparing the initial digital voltage signal to a predetermined normal range;

analyzing the initial digital voltage signal for a blood oxygenation level if the signal is below the predetermined range; and first reducing the analog current signal and converting the reduced analog current signal to a reduced digital voltage signal and then analyzing the reduced digital voltage signal for a blood oxygenation level if the initial digital voltage signal is greater than the predetermined normal range.

12. The method as defined in claim 11, wherein the step of reducing the analog current signal comprises reducing the analog current signal a variable amount.

13. The method as defined in claim 11, wherein the step of reducing the analog current signal comprises reducing the analog current signal a fixed amount.

14. An oximeter for non-invasively measuring arterial oxygen saturation, comprising:

a sensor including at least first and second light emitting devices for producing light in at least two wavelengths;

at least one photodetector for detecting said light, after passing through a tissue sample containing a pulsating blood supply, and for producing an analog electrical current signal representing the absorption of each wavelength of said light;

an analog to digital converter for converting said analog electrical current signal to a digital voltage signal; and a processing unit, the processing unit programmed to:

sample the digital voltage signal to provide a first vector comprising data samples representative of light absorbed of the first wavelength;

sample the digital voltage signal to provide a second vector comprising data samples representative of light absorbed of the second wavelength;

calculate a ratio of the first vector to the second vector; and use the ratio to determine arterial oxygen saturation.

15. The oximeter as defined in claim 14, wherein the processing unit is further programmed to adjust the range of the analog electrical current signal to an expected input range.

16. The oximeter as defined in claim 14, wherein the processing unit is further programmed to compare a predicted value of at least one of the first and second wavelengths to an observed value of the same wavelength and to determine a noise metric.

17. The oximeter as defined in claim 14, wherein the processing unit is further programmed to filter data with the noise metric.

18. The oximeter as defined in claim 14, wherein the processing unit is further programmed to synchronize the calculation with a cardiac pulse detection signal.

19. The oximeter as defined in claim 14, wherein the processing unit is programmed to calculate the ratio using a least square minimization method.

* * * * *